United States Patent

Nedelec et al.

[11] Patent Number: 4,464,302
[45] Date of Patent: Aug. 7, 1984

[54] 17-[(HYDROXYMETHYL)FORMAMIDO-METHYLENE]-STEROIDS

[75] Inventors: Lucien Nedelec, Le Raincy; Vesperto Torelli, Maisons-Alfort, both of France

[73] Assignee: Roussel Uclaf, Paris, France

[21] Appl. No.: 173,172

[22] Filed: Jul. 28, 1980

[30] Foreign Application Priority Data

Jul. 31, 1979 [FR] France .................. 79 19653

[51] Int. Cl.³ .............................. C07J 3/00
[52] U.S. Cl. ..................... 260/397.1; 260/239.55 C; 260/397.4; 260/397.45; 260/397.47; 260/397.5
[58] Field of Search ............... 260/397.1, 397.45; /Steroids MS File

[56] References Cited

U.S. PATENT DOCUMENTS 3,535,312 10/1970 Philippson et al. ............... 260/397.1
3,816,480 6/1974 Lenz ................................ 260/397.1

Primary Examiner—Elbert L. Roberts
Attorney, Agent, or Firm—Charles A. Muserlian

[57] ABSTRACT

Novel 17-[(hydroxymethyl)formamido methylene]-steroids of the formula

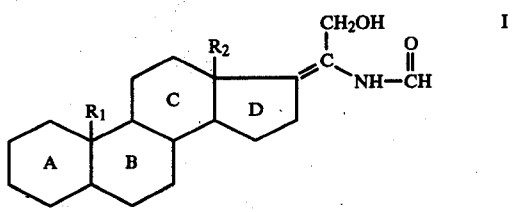

wherein $R_1$ is selected from the group consisting of hydrogen, alkyl of 1 to 4 carbon atoms optionally substituted with halogen or an oxygen or nitrogen function and alkenyl and alkynyl of 2 to 4 carbon atoms, $R_2$ is alkyl of 1 to 4 carbon atoms and the A,B,C and D rings may contain one or more double bonds and are optionally substituted with at least one member of the group consisting of hydroxy, keto, halogen, alkyl and alkoxy of 1 to 4 carbon atoms and alkenyl and alkynyl of 2 to 4 carbon atoms and a process for their preparation which are intermediates for the preparation of the corresponding 17-hydroxyacetyl steroids.

19 Claims, No Drawings

17-[(HYDROXYMETHYL)FORMAMIDO-METHYLENE]-STEROIDS

STATE OF THE ART

Chem. Berichte, Vol. 109, No. 12 (1976), p. 3964 describes compounds useful as starting materials for the process.

OBJECTS OF THE INVENTION

It is an object of the invention to provide the novel steroids of formula I and to provide a novel process for their preparation and novel intermediates.

It is a further object of the invention to provide a novel process for the preparation of 17-hydroxyacetyl steroids.

These and other objects and advantages of the invention will become obvious from the following detailed description.

THE INVENTION

The novel steroids of the invention are 17-[(hydroxymethyl)formamido methylene]-steroids of the formula

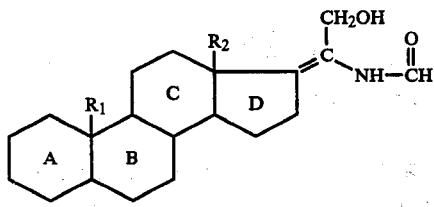

wherein $R_1$ is selected from the group consisting of hydrogen, alkyl of 1 to 4 carbon atoms optionally substituted with halogen or an oxygen or nitrogen function and alkenyl and alkynyl of 2 to 4 carbon atoms, $R_2$ is alkyl of 1 to 4 carbon atoms and the A,B,C and D rings may contain one or more double bonds and are optionally substituted with at least one member of the group consisting of hydroxy, keto, halogen, alkyl and alkoxy of 1 to 4 carbon atoms and alkenyl and alkynyl of 2 to 4 carbon atoms.

Examples of $R_1$ are alkyl such as methyl or ethyl; alkyl substituted with oxygen and nitrogen functions such as hydroxymethyl, hydroxyethyl, formyl, acetyl, cyano, aminomethyl and aminoethyl; haloalkyl such as halomethyl wherein the halogen is chlorine, bromine or fluorine; alkenyl such as vinyl the allyl; alkynyl such as ethynyl. Examples of $R_2$ are methyl and ethyl.

When the A,B,C and D rings contain one or more double bonds, the double bonds are preferably in 1(2), 3(4), 4(5) or 9(11) positions or a conjugated double bond system such as 3(4) and 5(6) or 4(5) and 6(7) or 1(2) and 4(5) or an aromatic system such as 1,3,5 positions or a triple bond system such as 1(2), 4(5), 6(7).

When the A,B,C and D rings are substituted with at least one hydroxy group they are preferably in the 3- and/or 11-positions. When the A,B,C and D rings are substituted with at least one keto groups, they are preferably in the 3- and/or 11-position. When the A,B,C and D rings contain at least one halogen, they are preferably fluorine, chlorine or bromine in the 6- and/or 9α-positions.

When the A,B,C and D rings are substituted with at least one alkyl, they are preferably methyl or ethyl in the 2,6,7,16α and/or 16β-positions. When the A,B,C and D rings are substituted with at least one alkoxy, they are methoxy or ethoxy in the 3-and/or 11β-positions. When the A,B,C and D rings are substituted with at least one alkenyl, they are preferably vinyl or allyl in the 11β-position. When the A,B,C and D rings are substituted with at least one alkynyl, they are preferably ethynyl in the 11β-position.

Among the preferred compounds of formula I are those wherein $R_2$ is methyl and those wherein $R_1$ is hydrogen or methyl.

Preferred compounds of the invention are those of the formula

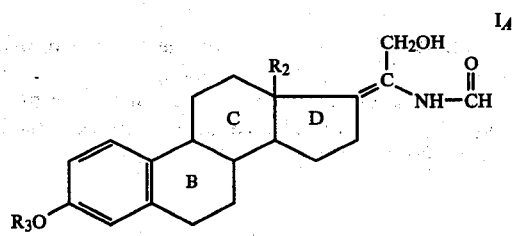

wherein $R_2$ is alkyl of 1 to 4 carbon atoms, $R_3$ is alkyl of 1 to 8 carbon atoms and the B,C and D rings optionally contain at least one double bond and are optionally substituted with at least one of the above indicated substituents. Preferably, the B,C and D rings are unsubstituted.

Other preferred compounds of the invention are those of the formula

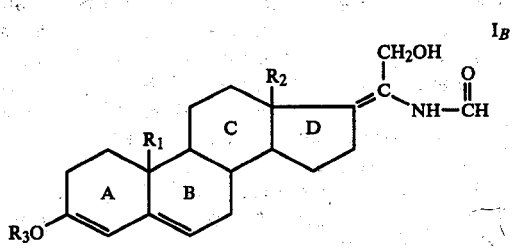

wherein $R_1$ and $R_2$ have the above definitions and $R_3$ is alkyl of 1 to 8 carbon atoms and the A,B,C and D rings optionally contain at least one supplementary double bond and are optionally substituted with at least one of the above substituents.

A most preferred group of compounds within formula $I_B$ includes compounds of the formula

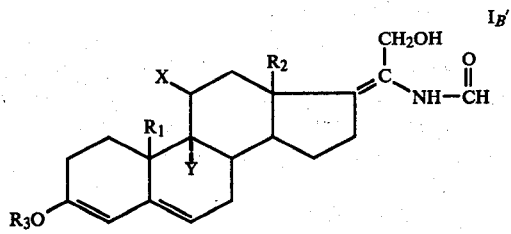

wherein $R_1$, $R_2$ and $R_3$ have the above definitions and X and Y are both hydrogen or together form a carbon-carbon double bond. Preferably, X and Y are hydrogen.

The compounds of formula I have a very great industrial interest as they are directly prepared from the corresponding 17-keto compounds in good yields by a simple and economical process and are able to be transferred directly into the corresponding 17-hydroxyacetyl compounds in very good yields in a simple and economical manner.

The compounds of formula I permit introduction of a hydroxyacetyl group beginning from 17-keto steroids in a rapid, simple and economical manner and it is a very generally applicable process for steroids having a ketone function in the 17-position. The compounds of formula I have in the 17-position the group

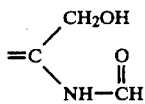

and the A,B,C and D rings and the nature and number of the substituents may be varied greatly.

The novel process of the invention for the preparation of a compound of formula I comprises reacting a compound of the formula

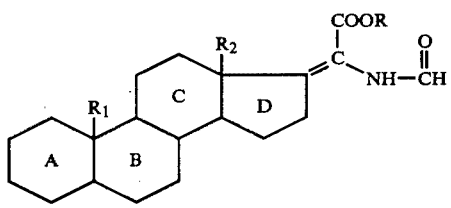

wherein $R_1$ and $R_2$ have the above definitions, R is alkyl of 1 to 18 carbon atoms and the A,B,C and D rings optionally contain at least one double bond and are optionally substituted with at least one of the above substituents with a reducing agent to obtain the corresponding compound of formula I. If the compounds of formula II possess a 3-keto or a 3-hydroxy group, it is protected respectively in the form of an enol ether or in the form of an ether.

The process of the invention for the preparation of a compound of formula $I_A$ comprises reacting a compound of the formula

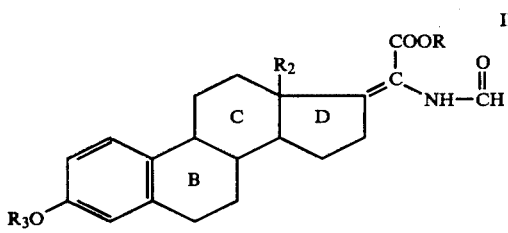

wherein R, $R_2$, $R_3$, B, C and D have the above definition with a reducing agent to obtain the corresponding compound of formula $I_A$. Particularly preferred starting compounds are the compounds of the formula

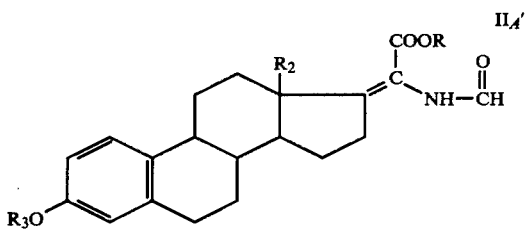

wherein R, $R_2$ and $R_3$ have the above definitions.

The process of the invention for the preparation of compounds of formula $I_B$ comprises reacting a compound of the formula

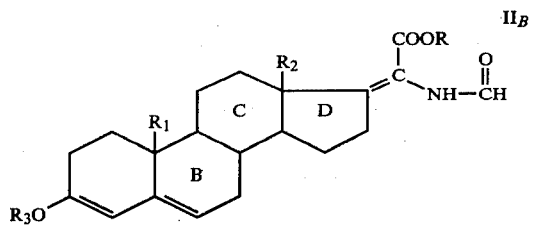

wherein R,$R_1$,$R_2$,$R_3$,B, C and D have the above definitions with a reducing agent to form the compound of formula $I_B$. A preferred starting compound has the formula

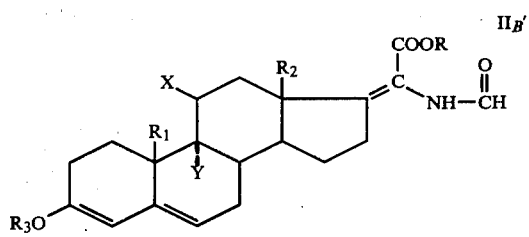

wherein R,$R_1$, $R_2$ and $R_3$ have the above definition and X and Y are both hydrogen or form a carbon-carbon double bond. Preferably, X and Y are hydrogen.

The reducing agent may be an aluminum hydride or an alkali metal dihydro bisalkoxy aluminate of the formula $$M-AlH_2(OAlk_1OAlk_2)_2$$

wherein M is an alkali metal and $Alk_1$ and $Alk_2$ are individually alkyl of 1 to 8 carbon atoms. Preferably, the reducing agent is lithium aluminum double hydride or sodium dihydro bis(2-methoxyethoxy) aluminate and the reduction is effected at a temperature near 0° C. such as −5° to 5° C. $R_3$ is preferably methyl or ethyl and R is preferably ethyl.

The starting compounds of formula II are novel products except for ethyl (20 E) formamido-3-methoxy-19-nor-$\Delta^{1,3,5(10),17(20)}$-pregnatetrene-21-oate which is described by Schöllkopf et al [Chem. Ber., Vol. 109 (1976), p. 3964]. The preferred intermediates of formula II are those wherein $R_1$ is hydrogen or methyl and $R_2$ is methyl.

The compounds of formula II may be prepared by reacting a compound of the formula $$\underset{M-CH-COOR}{\overset{NC}{|}}$$

wherein M is an alkali metal and R is alkyl of 1 to 18 carbon atoms with a compound of the formula

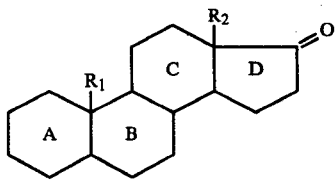

wherein $R_1$ and $R_2$ have the above definitions and the A,B,C and D rings optionally contain at least one double bond and are optionally substituted with at least one of the above discussed substituents. M is preferably potassium.

Another process of the invention comprises reacting a compound of formula I with an acid hydrolysis agent to form the corresponding compound of the formula

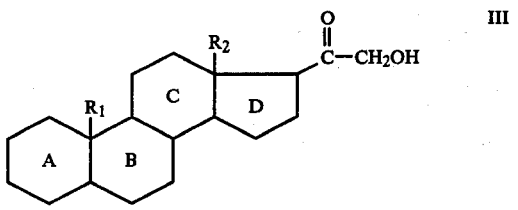

wherein $R_1$, $R_2$ and the A,B,C and D rings are as discussed above. The preferred acid hydrolysis agents are hydrochloric acid and sulfuric acid.

It is also possible to transform the compounds of formula II into the compounds of formula III without isolating the compounds of formula I and it is also a part of the invention to react a compound of formula II with a reducing agent to form a compound of formula I in situ which is then reacted with an acid hydrolysis agent.

The compounds of formula III have a very great industrial interest as they are known to be very useful pharmaceutical products such as corticosterone, 19-nor-corticosterone, desoxycorticosterone, 19-nor-desoxycorticosterone and 9(11)-dehydro-desoxycorticosterone.

In the following examples there are described several preferred embodiments to illustrate the invention. However, it should be understood that the invention is not intended to be limited to the specific embodiments.

EXAMPLE 1

3-methoxy-19-nor-$\Delta^{1,3,5(10)}$-pregnatriene-21-ol-3-one

STEP A: (20E) 20-formamido-3-methoxy-19-nor-$\Delta^{1,2,5(10),17(20)}$-pregnetetraene-21-ol A solution of 1.6 g of ethyl (20E) 20-formamido-3-methoxy-19-nor-$\Delta^{1,3,5(10),17(20)}$-pregnatetraene-21-oate [prepared by process of Schöllkopf et al, Chem. Ber., Vol. 19 (1976), p. 3964] in 32 ml of anhydrous tetrahydrofuran was stirred at 0° C. for 2 hours with 200 mg of lithium aluminum double hydride and 200 mg of potassium borohydride and then ethanol was added thereto dropwise to decompose excess lithium aluminum double hydride. The mixture was stirred at room temperature for one hour and was then diluted with a solution of Seignette salt (sodium potassium tartrate). The mixture was extracted with ethyl acetate and the organic phase was filtered. The filtrate was washed with water, dried and evaporated to dryness and the residue was triturated with isopropyl ether. The suspension was iced and was vacuum filtered. The product was washed with isopropyl ether and was dried in air to obtain 1.28 g of (20E) 20-formamido-3-methoxy-19-nor-$\Delta^{1,3,5(10),17(20)}$-pregnetetraene-21-ol which was used as is for the next step. A sample of the product after crystallization from methanol melted at 191° C.

STEP B: 3-methoxy-19-nor-$\Delta^{1,3,5(10)}$-pregnatriene-21-ol-20-one 1 ml of 5N hydrochloric acid was added to a suspension of 300 mg of the product of Step A in 10 ml of methanol and the mixture was stirred at room temperature for one hour. The mixture was then diluted with water and was filtered and the recovered product was washed with water and dried towards 50° C. to obtain 200 mg of 3-methoxy-19-nor$\Delta^{1,3,5(10)}$-pregnariene-21-ol-20-one. The filtrate was extracted with methylene chloride and the organic phase was evaporated to dryness to obtain another 70 mg of the desired product for a total yield of 97%. After crystallization from methanol, the product melted at 130°–131° C.

Analysis: $C_{21}H_{28}O_3$; molecular weight=328.455.

| Calculated: | % C 76.79 | % H 8.59 |
|---|---|---|
| Found: | 76.6 | 8.5 |

IR Spectrum (chloroform): Absorption at 3458 cm$^{-1}$ (associated OH); at 1706 cm$^{-1}$ (20-keto); at 1610, 1577 and 1500 cm$^{-1}$(aromatic).

Circular Dichroism (ethanol):

| Max. at 231 nm | $\Delta\epsilon = +2.3$ |
|---|---|
| Max. at 287 nm | $\Delta\epsilon = +3.4$ |

NMR Spectrum (CDCl$_3$): Peaks at 4.16–4.25 ppm (20-hydrogen); at 3.17–3.25–3.33 ppm (hydrogen of —OH).

EXAMPLE 2

$\Delta^4$-pregnene-21-ol-3,20-dione

STEP A: Ethyl (20E) 20-formamido-3-ethoxy-$\Delta^{3,5,17(20)}$-pregnatriene-21-oate A solution of 2.25 g of ethyl isocyanate in 20 ml of anhydrous tetrahydrofuran was added with stirring at −10° C. to a solution of 2.15 g of potassium tert.-butylate in 50 ml of anhydrous tetrahydrofuran and after 15 minutes of stirring the mixture, a solution of 5.025 g of 3-ethoxy-$\Delta^{3,5}$-androstadiene-17-one in 80 ml of anhydrous tetrahydrofuran was slowly added thereto. The temperature was allowed to return to room temperature and the mixture was stirred for 15 hours and was then poured into an aqueous saturated ammonium chloride solution. The mixture was extracted with ether and the organic phase was washed with water, dried and evaporated to dryness. The residue was chromatographed over silica gel and was eluted with a 1-1 benzene-ethyl acetate mixture to obtain a first fraction of 4.71 g (69% yield) of ethyl (20E) 20-formamido-3-ethoxy-$\Delta^{3,5,17(20)}$-pregnatriene-21-oate and 0.97 g (14% yield) of the corresponding (Z) isomer. After crystallization from methanol, the E isomer melted of 204° C. and the Z isomer melted at 172° C.

STEP B: (20E) 20-formamido-3-ethoxy-$\Delta^{3,5,17(20)}$-pregnatriene-21-ol 150 mg of lithium aluminum double hydride were added in a plurality of small portions with stirring to a solution of 1.025 g of the (20E) isomer of Step A in 20 ml of anhydrous tetrahydrofuran in an ice bath and the temperature was then allowed to rise to room temperature. The mixture was stirred for 15 hours and 5 ml of ethanol were cautiously added thereto to destroy excess lithium aluminum double hydride to obtain a solution of (20E) 20-formamido-3-ethoxy-$\Delta^{3,5,17(20)}$-pregnatriene-21-ol which was used for the next step.

STEP C: $\Delta^4$-pregnene-21-ol-3,20-dione

The reaction mixture of Step B and 5 ml of 5N hydrochloric acid were stirred at room temperature for 6 hours and the mixture was diluted with water. The mixture was extracted with ethyl acetate and the organic phase was washed with water, dried and evaporated to dryness to obtain 600 mg of $\Delta^4$-pregnene-21-ol-3,20-dione which melted at 141°–142° C. after crystallization from a methylene chloride-isopropyl ether mixture.

EXAMPLE 3

3-methoxy-19-nor-$\Delta^{1,3,5(10)}$-pregnatriene-21-ol-20-one

STEP A: (20E) 20-formamido-3-methoxy-19-nor-$\Delta^{1,3,5(10),17(20)}$-pregnatetraene-21-ol 3.5 ml of a 70% benzene solution of sodium dihydro bis-(2-methoxy ethoxy) aluminate were added over 10 minutes under nitrogen to a solution of 1.4 g of ethyl (20E) 20-formamido-3-methoxy-19-nor-$\Delta^{1,3,5(10),17(20)}$-pregnatetraene-21-oate in 30 ml of anhydrous tetrahydrofuran cooled in an ice bath and the mixture was stirred for one hour. Excess hydride was destroyed by careful addition of 10 ml of ethanol and then 0.35 g of potassium borohydride was added thereto. The reaction mixture was stirred for one hour to obtain a mixture containing (20E) 20-formamido-3-methoxy-19-nor-$\Delta^{1,3,5(10),17(20)}$-pregnatetraene-21-ol which was used for the next step.

STEP B: 3-methoxy-19-nor-$\Delta^{1,3,5(10)}$-pregnatriene-21-ol-20-one

The mixture of Step A was acidified with 20 ml of 5N hydrochloric acid and was then stirred for 15 hours at room temperature and was diluted with water. The mixture was extracted with ethyl acetate and the organic phase was washed with water, dried and evaporated to dryness. The residue was chromatographed over silica gel and was eluted with a 9-1 benzene-ethyl acetate mixture to obtain 0.95 g of 3-methoxy-19-nor-$\Delta^{1,3,5(10)}$-pregnatriene-21-ol-20-one in the form of colorless crystals melting at 130°–131° C.

EXAMPLE 4

2,2-dimethyl-13$\beta$-ethyl-18,19-dinor-$\Delta^4$-pregnene-21-ol-3,20-dione

STEP A: 2,2-dimethyl-13$\beta$-ethyl-17$\beta$-[2'(RS)-tetrahydropyranyloxy)]-$\Delta^4$-gonene-3-one 20 ml of a solution of 1.4M potassium tert.-butylate in tetrahydrofuran were added dropwise over one hour with stirring under an inert atmosphere to a mixture of 1.860 g of 13$\beta$-ethyl-17$\beta$-[2'(RS)-tetrahydropyranyloxy]-$\Delta^4$-gonene-3-one [described in U.S. Pat. No. 3.338.928], 10 ml of tetrahydrofuran and 4 ml of methyl iodide cooled to −70° C. and the mixture was stirred at −70° C. for 30 minutes and was then poured into an aqueous saturated ammonium chloride solution. The mixture was extracted with methylene chloride and the organic phase was dried and evaporated to dryness to obtain 2.2 g of raw 2,2-dimethyl-13$\beta$-ethyl-17$\beta$-[2'(RS)-tetrahydropyranyloxy]-$\Delta^4$-gonene-3-one.

STEP B: 2,2-dimethyl-13$\beta$-ethyl-$\Delta^4$-gonene-17$\beta$-ol-3-one

A solution of 2.2 g of the product of Step A, 20 ml of ethanol and 4 ml of 2N hydrochloric acid was refluxed for one hour, cooled and poured into water. The mixture was extracted with methylene chloride and the organic phase was washed with water, dried and evaporated to dryness under reduced pressure. The residue was crystallized from isopropyl ether to obtain 735 mg of 2,2-dimethyl-13$\beta$-ethyl-$\Delta^4$-gonene-17$\beta$-ol-3-one melting at 168° C. The mother liquors were evaporated to dryness and the residue was chromatographed over silica gel. Elution with an 8-2 benzene-ethyl acetate mixture yielded 375 mg of product which was crystallized from isopropyl ether to obtain 290 mg of product melting at 169° C. The product was chromatographed over silica gel and was eluted with isopropyl ether-methylene chloride mixture to obtain 2,2-dimethyl-13$\beta$-ethyl-$\Delta^4$-gonene-17$\beta$-ol-3-one melting at 170° C.

STEP C: 2,2-dimethyl-13$\beta$-ethyl-$\Delta^4$-gonene-3,17-dione 2.6 ml of Heilbron Jones solution were added dropwise at 0° C. to a solution of 2.475 g of the product of Step B in 50 ml of acetone and the mixture was stirred for 15 minutes at 0° C. 1 ml of methanol was added to the mixture which was then diluted with water and was vacuum filtered. The product was washed with water to obtain 2.380 g of 2,2-dimethyl-13$\beta$-ethyl-$\Delta^4$-gonene-3,17-dione melting at 195° C.

STEP D: 2,2-dimethyl-3-ethoxy-13$\beta$-ethyl-$\Delta^{3,5}$-gonadiene-17-one 0.25 ml of a solution of 0.2% sulfuric acid in ethanol was added to a mixture of 1 g of the product of Step C, 10 ml of anhydrous ethanol and 1 ml of ethyl orthoformate and the mixture was refluxed under an inert atmosphere for 70 minutes and was then cooled. A few drops of triethylamine were added to the mixture which was diluted with aqueous sodium bicarbonate and was extracted with ether. The ether phase was washed with water, dried and evaporated to dryness under reduced pressure to obtain 1.250 g of residue. The latter was chromatographed over silica gel and was eluted with a 95-5 benzene-ethyl acetate mixture to obtain 0.95 g of 2,2-dimethyl-3-ethoxy-13$\beta$-ethyl-$\Delta^{3,5}$-gonadiene-17-one which was used as is for the next step.

STEP E: Mixture of E and Z isomers of ethyl 2,2-dimethyl-3-ethoxy-13$\beta$-ethyl-20-formamido-18,19-dinor-$\Delta^{3,5,17(20)}$-pregnatriene-21-oate 5.25 ml of ethyl isocyanoacetate were added dropwise under an inert atmosphere to a mixture of 3.36 g of the product of Step D, 15 ml of dioxane and 50 ml of 0.93M potassium tert.-butylate in dioxane and the mixture was heated at 80° C. for 75 minutes and was cooled. The mixture was poured into aqueous monosodium phosphate solution and was extracted with ethyl acetate. The organic phase was washed with water, dried and evaporated to dryness under reduced pressure. The residue was chromatographed over silica gel and was eluted with a 9-1 benzene-ethyl acetate mixture and then with a 7-3 mixture to obtain 3.9 g of mixture of E and Z isomers of ethyl 2,2-dimethyl-3-ethoxy-13$\beta$-ethyl-20-formamido-18,19-dinor-$\Delta^{3,5,17(20)}$-pregnatriene-21-oate.

STEP F: 2,2-dimethyl-3-ethoxy-13$\beta$-ethyl-20-formamido-18,19-dinor-$\Delta^{3,5,17(20)}$-pregnatriene-21-ol 125 mg of lithium aluminum double hydride were added to a solution of 850 mg of the product of Step E in 8.5 g of tetrahydrofuran cooled to 0° to −2° C. and the mixture was held at 0° C. for one hour. Then, 8.5 ml of ethanol and 125 mg of sodium borohydride were carefully added to the mixture which was then stirred at room temperature for 15 minutes and was diluted with ethyl acetate. An aqueous saturated sodium chloride solution was slowly added to the mixture to obtain a paste and the organic phase was decanted. The residue was taken up twice in ethyl acetate and the organic phase was washed with saturated sodium chloride aqueous solution, dried and evaporated to dryness under reduced pressure to obtain 710 mg of E and Z isomers of 2,2-dimethyl-3-ethoxy-13$\beta$-ethyl-20-formamido-18,19-dinor-$\Delta^{3,5,17(20)}$-pregnatriene-21-ol.

STEP G: 2,2-dimethyl-13$\beta$-ethyl-18,19-dinor-$\Delta^4$-pregnene-21-ol-3,20-dione 2.8 ml of 2N hydrochloric acid were added to a solution of 710 mg of the product of Step F in 14 ml of methanol and the mixture was allowed to stand at room temperature for 20 hours. The mixture was diluted with water and was extracted with methylene chloride. The organic phase was washed with aqueous sodium bicarbonate solution, then with water, dried and evaporated to dryness under reduced pressure to obtain 525 mg of residue. The latter was chromatographed over silica gel and was eluted with an 8-2 benzene-ethyl acetate mixture to obtain 340 mg of 2,2-dimethyl-13$\beta$-ethyl-18,19-dinor-$\Delta^4$-pregnene-21-ol-3,20-dione which was crystallized.

EXAMPLE 5

10$\beta$-ethynyl-19-nor-$\Delta^{4,9(11)}$-pregnadiene-21-ol-3,20-dione

STEP A: 3,3-ethylenedioxy-10$\beta$-ethynyl-$\Delta^{9(11)}$-estrene-5$\alpha$,17$\beta$-diol 8.24 g of lithium acetylide in ethylene diamine were added with stirring to a mixture of 4.12 g of 3,3-ethylenedioxy-5$\alpha$,10$\alpha$-epoxy-17$\beta$-benzyloxy-$\Delta^{9(11)}$-estrene (described in French Pat. No. 1,550,974) in 60 ml of ethylene diamine and the mixture was heated at 45° C. under inert atmosphere for 24 hours. The mixture was cooled in ice and was extracted with methylene chloride. The organic phase was washed with water, dried and evaporated to dryness. The residue was chromatographed over silica gel and was eluted with a 7-3 benzene-ethyl acetate mixture to obtain 3 g of 3,3-ethylenedioxy-10$\beta$-ethynyl-$\Delta^{9(11)}$-estrene-5$\alpha$,17$\beta$-diol which melted at 213° C. after crystallization from aqueous ethanol.

STEP B: 3,3-ethylenedioxy-10$\beta$-ethynyl-$\Delta^{9(11)}$-estrene-5$\alpha$-ol-17-one 4.5 g of pyridinium chlorochromate [Tetrahedron Letters, No. 31 (1975), p. 2647-2650] were added to a solution of 3 g of the raw product of Step A in 75 ml of methylene chloride containing 1% of pyridine and the mixture was stirred for one hour at room temperature. The mixture was chromatographed over silica gel and was eluted with ether to obtain 2.73 g of product. The latter was crystallized from aqueous ethanol, was washed and dried to obtain 2.43 g of 3,3-ethylenedioxy-10$\beta$-ethynyl-$\Delta^{9(11)}$-estrene-5$\alpha$-ol-17-one melting at 188° C.

STEP C: Ethyl 3,3-ethylenedioxy-10$\beta$-ethynyl-20-formamido-19-nor-$\Delta^{9(11),17(20)}$-pregnadiene-5$\alpha$-ol-21-oate 10.3 ml of 1.75M potassium tert.-butylate in tetrahydrofuran and 2 ml of ethyl isocyanacetate were added with stirring under an inert atmosphere to a solution of 2.14 g of the product of Step B in 21 ml of tetrahydrofuran and the mixture was stirred at room temperature for one hour and was then poured into ice water. The mixture was extracted with methylene chloride and the organic phase was washed with water, dried and evaporated to dryness under reduced pressure to obtain 3.7 g of ethyl 3,3-ethylenedioxy-10$\beta$-ethynyl-20-formamido-19-nor-$\Delta^{9(11),17(20)}$-pregnadiene-5$\alpha$-ol-21-oate.

STEP D: 3,3-ethylenedioxy-10$\beta$-ethynyl-20-formamido-19-nor-$\Delta^{9(11),17(20)}$-pregnadiene-5,21-diol 600 mg of lithium aluminum double hydride were added under an inert atmosphere in fractions with stirring at 5° C. to a solution of 3.7 g of the product of Step C in 90 ml of tetrahydrofuran and after stirring the mixture for 2 hours, ethanol was slowly added thereto to destroy excess hydride. 30 ml of ethanol were added and 0.5 g of sodium borohydride was added after which the suspension was stirred at room temperature for 20 minutes. 100 ml of ethyl acetate were added thereto followed by dropwise addition of aqueous sodium chloride solution to precipitate mineral salts in the form of a gummy residue. The organic phase was decanted and the residue was taken up twice in ethyl acetate. The combined organic phases were dried and evaporated to dryness to obtain 2.8 g of 3,3-ethylenedioxy-10$\beta$-ethynyl-20-formamido-19-nor-$\Delta^{9(11),17(20)}$-pregnadiene-5,21-diol.

STEP E: 10$\beta$-ethynyl-19-nor-$\Delta^{4,9(11)}$-pregnadiene-21-ol-3,20-dione A solution of 2.68 g of the product of Step D in 36 ml of methanol containing 3.6 ml of 6N hydrochloric acid was refluxed for 80 minutes and was cooled and diluted with ice water. The mixture was extracted with methylene chloride and the organic phase was dried and evaporated to dryness under reduced pressure. The residue was chromatographed over silica gel and was eluted with a 7-3 cyclohexane-ethyl acetate mixture. Different fractions were crystallized from a methylene chloride-isopropyl ether mixture to obtain 1.03 g of 10$\beta$-ethynyl-19-nor-$\Delta^{4,9(11)}$-pregnadiene-21-ol-3,20-dione melting at 162° C.

NMR Spectrum (CDCl$_3$): Peaks at 0.68 ppm (18—CH$_3$); at 2.23 ppm (C≡CH); at 4.21 ppm (21—CH$_2$); at 5.71–5.77–5.81 ppm (11-hydrogen); at 5.91 ppm (4-hydrogen).

EXAMPLE 6

19-nor-$\Delta^4$-pregnene-21-ol-3,20-dione

STEP A: Ethyl (20E) 3-ethoxy-20-formamido-19-nor-$\Delta^{3,5,17(20)}$-pregnatriene-21-oate A solution of 5 g of ethyl isocyanacetate in 30 ml of tetrahydrofuran was added at 10° C. over 15 minutes to a solution of 5 g of potassium tert.-butylate in 60 ml of tetrahydrofuran and the mixture was stirred for 10 minutes. A solution of 9 g of 3-ethoxy-$\Delta^{3,5}$-estradiene-17-one [described in U.S. Pat. No. 3,029,261] in 120 ml of tetrahydrofuran was added thereto and the mixture was stirred at room temperature for 4 hours and was poured into an aqueous saturated ammonium chloride solution. The mixture was extracted with ethyl acetate and the organic phase was washed with water, dried and evaporated to dryness under reduced pressure. The residue was crystallized from 20 ml of ether to obtain 10.9 g of ethyl (20E) 3-ethoxy-20-formamido-19-nor-$\Delta^{3,5,17(20)}$-pregnatriene-21-oate melting at 165° C.

| U.V. Spectrum (ethanol): | | |
|---|---|---|
| Max. with 238 nm | $E_1^1 = 725$ | $\epsilon = 30,000$ |
| U.V. Spectrum (0.1NHCl in ethanol): | | |
| Max. at 238 nm | $E_1^1 = 658$ | $\epsilon = 27,200$ |

STEP B: (20E) 3-ethoxy-20-formamido-19-nor-$\Delta^{3,5,17(20)}$-pregnatriene-21-ol 1.2 g of lithium aluminum double hydride and 1 g of sodium borohydride were added at 5° C. to a solution of 5.5 g of ethyl (20E) 3-ethoxy-20-formamido-19-nor-$\Delta^{3,5,17(20)}$-pregnatriene-21-oate in 100 ml of tetrahydrofuran and the mixture was stirred for 2 hours at 5° C. Then, 30 ml of ethanol were added thereto dropwise and the mixture was stirred at room temperature for 30 minutes. 20 ml of a solution of sodium potassium tartrate were added to the mixture which caused a precipitate in the solution and the surnageant was decanted. The precipitate was taken up several times in ethyl acetate and the combined organic phases were washed with aqueous saturated sodium chloride solution, dried and evaporated to dryness under reduced pressure. The residue was empasted with isopropyl ether and the mixture was vacuum filtered to obtain 4.3 g of (20E) 3-ethoxy-20-formamido-19-nor-$\Delta^{3,5,17(20)}$-pregnatriene-21-ol melting at 202° C.

| U.V. Spectrum (ethanol): | | |
|---|---|---|
| Max. at 239 nm | $E_1^1 = 668$ | $\epsilon = 24,800$ |

STEP C: 19-nor-$\Delta^4$-pregnene-21-ol-3,20-dione

A solution of 200 mg of the product of Step B, 5 ml of methanol and 1 ml of 5N hydrochloric acid was stirred at room temperature for one hour and was then poured into aqueous saturated sodium bicarbonate solution. The mixture was extracted with ethyl acetate and the organic phase was dried and evaporated to dryness under reduced pressure. The residue was empasted with ether and the mixture was vacuum filtered to obtain 160 mg of 19-nor-$\Delta^4$-pregnene-21-ol-3,20-dione melting at 132° C. After crystallization from isopropanol, the product melted at 133° C.

| U.V. Spectrum (ethanol): | | |
|---|---|---|
| Max. at 240–241 nm | $E_1^1 = 574$ | $\epsilon = 18,200$ |
| Inflex. towards 290 nm | $E_1^1 = 4$ | |

EXAMPLE 7

9α-fluoro-$\Delta^4$-pregnene-11β,21-diol-3,20-dione

STEP A: Ethyl (20E) 3-ethoxy-9α-fluoro-20-formamido-$\Delta^{3,5,17(20)}$-pregnatriene-11β-ol-21-oate A solution of 5.7 g of ethyl isocyanacetate in 57 ml of tetrahydrofuran was added dropwise with stirring under an inert atmosphere over 15 minutes to a solution of 5.789 g of potassium tert.-butylate in 202 ml of tetrahydrofuran cooled to 0° to 5° C. and the mixture was stirred at 0° to 5° C. for 15 minutes. A solution of 6 g of 3-ethoxy-9α-fluoro-$\Delta^{3,5}$-androstadiene-11β-ol-17-one [described in U.S. Pat. No. 3,968,132] in 120 ml of tetrahydrofuran was added thereto over 10 minutes and the mixture stood for 3¼ hours at room temperature. The mixture was cooled to 5° to 10° C. and 200 ml of an aqueous saturated sodium chloride solution were added thereto. The mixture was extracted with ethyl acetate and the organic phase was washed with aqueous saturated sodium chloride solution, dried and evaporated to dryness. The residue was chromatographed over silica gel and was eluted with a 95-5 chloroform-methanol mixture to obtain 5.9 g of ethyl (20E) 3-ethoxy-9α-fluoro-20-formamido-$\Delta^{3,5,17(20)}$-pregnatriene-11β-ol-21-oate.

I.R. Spectrum (ethanol):

| Max. at 239 nm | $E_1^1 = 625$ | $\epsilon = 28,800$ |
|---|---|---|

STEP B: (20E) 3-ethoxy-9α-fluoro-20-formamido-$\Delta^{3,5,17(20)}$-pregnatriene-11β,21-diol 2 g of lithium aluminum double hydride were added in small fractions over 15 minutes at 0° to 5° C. to a solution of 4 g of the product of Step A in 80 ml of tetrahydrofuran and the mixture was stirred at 0° to 5° C. for 90 minutes. 4 ml of aqueous saturated ammonium chloride solution were added dropwise to the mixture which was then vacuum filtered and the filter was washed with a 7-3 chloroform-methanol mixture. The filtrate was evaporated to dryness to obtain 2.070 g of residue. The latter was chromatographed over silica gel and was eluted with a 95-5 chloroform-methanol mixture containing 0.5°/°/$_{oo}$ triethylamine to obtain (20I 3-ethoxy-9α-fluoro-20-formamido-$\Delta^{3,5,17(20)}$-pregnatriene-11β,21-diol.

| U.V. Spectrum (ethanol): | | |
|---|---|---|
| Max. at 238–239 nm | $E_1^1 = 492$ | $\epsilon = 20,600$ |

STEP C: 9α-fluoro-$\Delta^4$-pregnene-11β,21-diol-3,20-dione

Using the procedure of Step C of Example 6, the product of Step B was reacted to obtain 9α-fluoro-$\Delta^4$-pregnene-11β,21-diol-3,20-dione.

EXAMPLE 8

$\Delta^4$-pregnene-11β,21-diol-3,20-dione

STEP A: ethyl (20E) 3-ethoxy-20-formamido-$\Delta^{3,5,17(20)}$-pregnatriene-11-one-21-oate A solution of 15.8 ml of ethyl isocyanacetate in 95 ml of tetrahydrofuran was added over 10 minutes with stirring under an inert atmosphere to a solution of 16.21 g of potassium tert.-butylate in 145 ml of tetrahydrofuran cooled to 0° to 5° C. and the mixture was stirred for 20 minutes at 0° to 5° C. A solution of 23.8 g of 3-ethoxy-$\Delta^{3,5}$-androstadiene-11,17-dione [described in U.S. Pat. No. 3,055,917] in 130 ml of tetrahydrofuran was added to the mixture and after stirring the mixture at 0° to 5° C. for 45 minutes, 500 ml of aqueous saturated ammonium chloride solution were added thereto. The mixture was extracted with ethyl acetate and the organic phase was washed with aqueous saturated ammonium chloride solution, dried and evaporated to dryness under reduced pressure. The residue was taken up in 100 ml of methylene chloride and the mixture was filtered. 500 ml of ethyl acetate were added to the filtrate and the methylene chloride was distilled off under reduced pressure. The mixture was iced and vacuum filtered and the product was washed with ethyl acetate to obtain 23.7 g of ethyl (20E) 3-ethoxy-20-formamido-$\Delta^{3,5,17(20)}$-pregnatriene-11-one-21-oate melting at 218° C. The mother liquors were chromatographed over silica gel and were eluted with a 7-3 benzene-ethyl acetate mixture. The product was crystallized from ethyl acetate to obtain another 4.814 g of the said product melting at 218° C.

STEP B: (20E) 3-ethoxy-20-formamido-$\Delta^{3,5,17(20)}$-pregnatriene-11β,21-diol 2.266 g of potassium borohydride were added at 0° to 5° C. to a solution of 10 g of the product of Step A in 200 ml of tetrahydrofuran and then 2.266 g of lithium aluminum double hydride were added thereto in small fractions over 10 minutes. The mixture was stirred for 110 minutes at 0° to 5° C. under an inert atmosphere and then 10 ml of ethanol were carefully added thereto over 30 minutes. The mixture was stirred at 0° to 5° C. for 30 minutes and the temperature was allowed to rise over 30 minutes. 10 ml of aqueous saturated ammonium chloride solution were added to the mixture which was then vacuum filtered. The filtrate was washed with chloroform and evaporated to dryness under reduced pressure to obtain 9 g of (20E) 3-ethoxy-20-formamido-$\Delta^{3,5,17(20)}$-pregnatriene-11$\beta$,21-diol.

| U.V. Spectrum (ethanol): | | |
|---|---|---|
| Max. at 237 nm | $E_1^1 = 540$ | $\epsilon = 21,700$ |

STEP C: $\Delta^4$-pregnene-11$\beta$,21-diol-3,20-dione

Using the procedure of Step C of Example 6, the product of Step B was reacted to obtain $\Delta^4$-pregnene-11$\beta$,21-diol-3,20-dione.

Various modifications of the products and processes of the invention may be made without departing from the spirit or scope thereof and it is to be understood that the invention is intended to be limited only as defined in the appended claims.

We claim:

1. 17-[(hydroxymethyl)formamido-methylene]-steroids of the formula

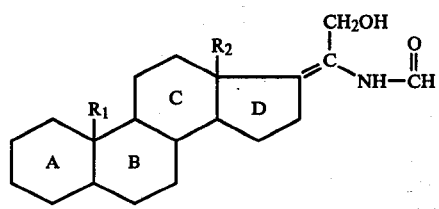

wherein $R_1$ is selected from the group consisting of hydrogen, alkyl of 1 to 4 carbon atoms optionally substituted with a member selected from the group consisting of halogen, hydroxy and amino, and alkenyl and alkynyl of 2 to 4 carbon atoms, $R_2$ is alkyl of 1 to 4 carbon atoms and the A,B,C and D rings may contain one or more double bonds and are optionally substituted with at least one member of the group consisting of hydroxy, keto, halogen, alkyl and alkoxy of 1 to 4 carbon atoms and alkenyl and alkynyl of 2 to 4 carbon atoms.

2. A compound of claim 1 wherein $R_2$ is methyl.

3. A compound of claim 1 wherein $R_1$ is selected from the group consisting of hydrogen and methyl.

4. A compound of claim 1 having the formula

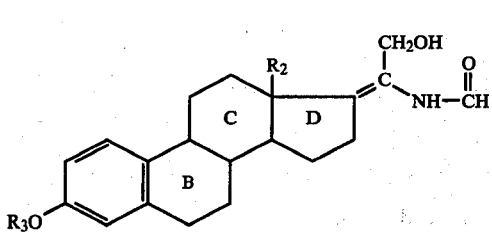

wherein $R_2$ is alkyl of 1 to 4 carbon atoms, $R_3$ is alkyl of 1 to 8 carbon atoms and the B,C and D rings optionally contain at least one double bond and are optionally substituted with at least one substituent of claim 1.

5. A compound of claim 4 wherein the B,C and D rings are unsubstituted.

6. A compound of claim 1 having the formula

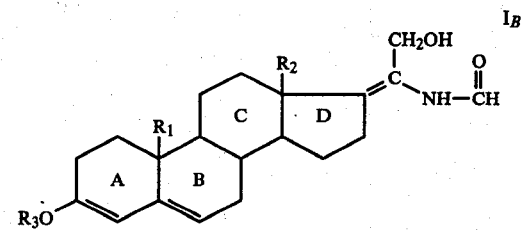

wherein $R_1$ and $R_2$ have the definition of claim 1, $R_3$ is alkyl of 1 to 8 carbon atoms and the A,B,C and D rings optionally contain at least one supplementary double bond and are optionally substituted with at least one of the substituents of claim 1.

7. A compound of claim 6 having the formula

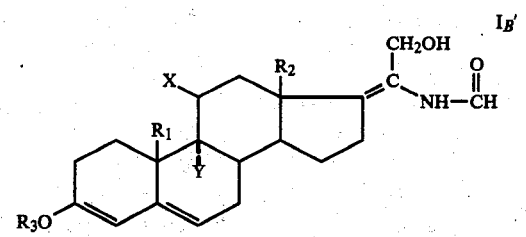

wherein $R_1$, $R_2$ and $R_3$ have the definitions of claim 6 and X and Y are both hydrogen or form a carbon-carbon double bond.

8. A compound of claim 7 wherein X and Y are hydrogen.

9. A process for the preparation of a compound of claim 1 comprising reacting a compound of the formula

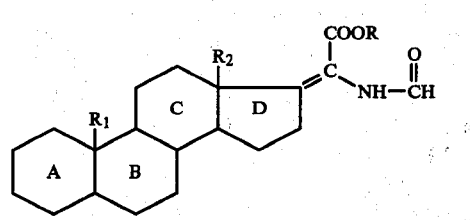

wherein $R_1$ and $R_2$ have the above definition, R is alkyl of 1 to 18 carbon atoms and the A,B,C and D rings optionally contain at least one double bond and are optionally substituted with at least one of the above substituents, defined in claim 1 with a reducing agent selected from the group consisting of an aluminum hydride and an alkali metal dihydro bisalkoxy aluminate of the formula

M-AlH$_2$(OAlk$_1$OAlk$_2$)$_2$ wherein M is an alkali metal and Alk$_1$ and Alk$_2$ are individually alkyl of 1 to 8 carbon atoms to obtain the corresponding compound of claim 1.

10. The process of claim 9 wherein the starting compounds has a 3-hydroxyl group protected in the form an ether or a 3-keto group protected in the form of an enol ether.

11. The process of claim 9 wherein the starting compound has the formula

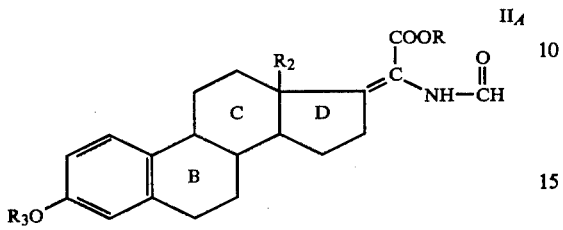

II$_A$ wherein R$_2$, R$_3$, B, C and D have the definition of claim 4 and R has the definition of claim 9.

12. The process of claim 11 wherein the starting compound has the formula

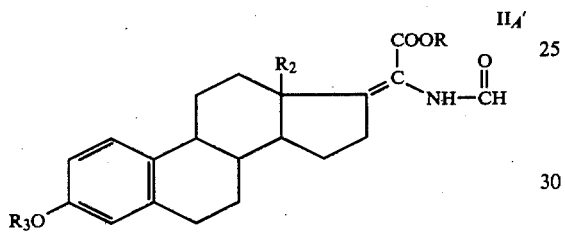

II$_A'$ wherein R, R$_2$ and R$_3$ have the definitions of claim 11.

13. The process of claim 9 wherein the starting compound has the formula

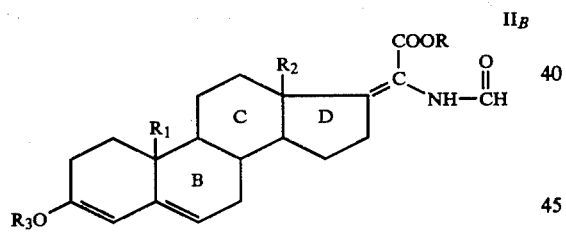

II$_B$ wherein R, R$_1$, R$_2$, B, C and D have the definitions of claim 9 and R$_3$ has the definition of claim 11.

14. The process of claim 13 wherein the starting compound has the formula

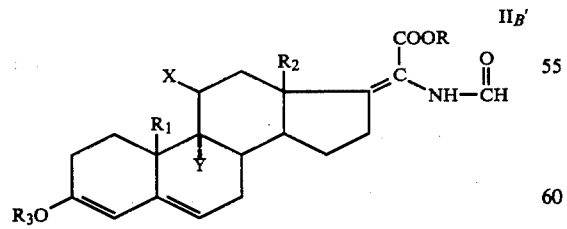

II$_B'$ wherein R, R$_1$, R$_2$ and R$_3$ have the above definitions and X and Y are both hydrogen or form a carbon-carbon double bond.

15. The process of claim 14 wherein X and Y are hydrogen.

16. A compound of the formula

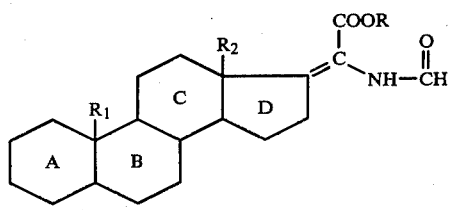

II wherein R$_1$, R$_2$, A,B,C and D have the definitions of claim 1 and R is alkyl of 1 to 18 carbon atoms, except ethyl (20E) 20-formamido-3-methoxy-19-nor-$\Delta^{1,3,5(10),17(20)}$-pregnatetraene-21-oate.

17. A compound of claim 16 wherein R$_1$ is hydrogen or methyl and R$_2$ is methyl.

18. A process comprising reacting a compound of claim 1 with an acid hydrolysis agent to obtain the corresponding compound of the formula

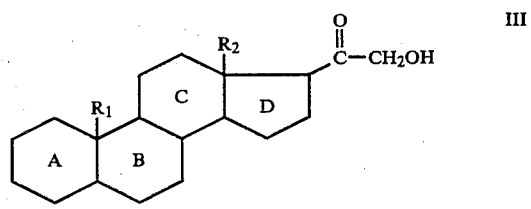

III

19. A process comprising reacting a compound of the formula

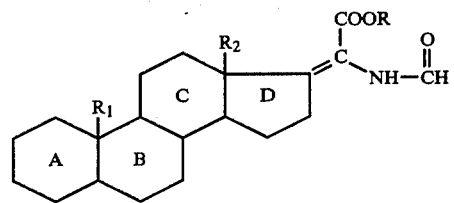

wherein R$_1$ and R$_2$ have the definitions of claim 1, R is alkyl of 1 to 18 carbon atoms and the A,B,C and D rings optionally contain at least one double bond and are optionally substituted with at least one of the substituents defined in claim 1, with a reducing agent selected from the group consisting of an aluminum hydride and an alkali metal dihydro bisalkoxy aluminate of the formula M-AlH$_2$(OAlk$_1$OAlk$_2$)$_2$ wherein M is an alkali metal and Alk$_1$ and Alk$_2$ are individually alkyl of 1 to 8 carbon atoms to obtain in situ the corresponding compound of claim 1 and reacting the latter with an acid hydrolysis agent to obtain the corresponding compound of the formula

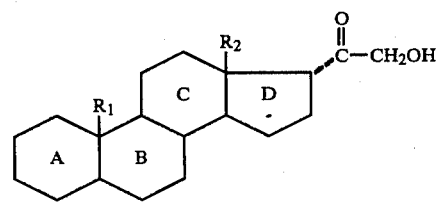

as defined in claim 18.

* * * * *